United States Patent [19]

Lawton

[11] Patent Number: 4,567,019

[45] Date of Patent: Jan. 28, 1986

[54] COLOR REVERSING COMPOSITIONS

[75] Inventor: William R. Lawton, Orchard Park, N.Y.

[73] Assignee: Graphic Controls Corporation, Buffalo, N.Y.

[21] Appl. No.: 796,012

[22] Filed: May 11, 1977

[51] Int. Cl.$^4$ .................. G01N 31/22; C09K 3/00
[52] U.S. Cl. ........................... 422/57; 116/216; 374/163; 436/2; 252/408.1; 428/913
[58] Field of Search ............ 252/408.1; 428/913, 428/411; 116/207, 216; 374/162, 163; 436/2; 422/56, 57

[56] References Cited

U.S. PATENT DOCUMENTS

| | | | |
|---|---|---|---|
| 3,389,007 | 6/1968 | Oda | 117/36.2 |
| 3,445,261 | 5/1969 | Talvalkar | 117/36.9 |
| 3,674,535 | 7/1972 | Blose | 428/913 X |
| 3,751,286 | 8/1973 | Newman | 428/913 X |
| 3,895,173 | 7/1975 | Adachi | 428/913 X |
| 3,916,068 | 10/1975 | Kohmura | 428/411 |
| 4,138,357 | 2/1979 | Igarashi | 374/162 X |

Primary Examiner—Edward A. Miller
Assistant Examiner—Catherine S. Kilby
Attorney, Agent, or Firm—Michael G. Berkman

[57] ABSTRACT

Heat-sensitive compositions which rapidly develop color upon heating and rapidly discharge their color upon cooling, comprising an intimate mixture of a 3,3-bis (p-aminophenyl) phthalide and an organic acid. The color-producing and color-discharging cycle may be reproduced many times without noticeable change in response. The novel compositions of the invention are useful as temperature indicators, thermal display media, safety papers and validation devices.

8 Claims, No Drawings

COLOR REVERSING COMPOSITIONS

This invention relates to compositions which are sensitive to heat, forming color on application of heat and having the color thus formed discharged on removal of the heat source.

Many compounds known as having thermochromic properties change color on application of heat and revert to their original color upon cooling. Day has discussed thermochromic materials and thermochromism in a number of reviews, e.g., Chemical Reviews, Volume 63, pp. 65–80 (1963) and Volume 68, pp. 649–658 (1968). The use of thermochromic materials for display has been described by Flint et al. in NASA Report, 1969, NASA CR 86136; by Teeg and Hallman, U.S. Pat. No. 3,438,022 and U.S. Pat. No. 3,365,577; by Baum, U.S. Pat. No. 3,293,055 and by Keith, U.S. Pat. No. 3,396,378. Thermochromic materials have also been described as useful for temperature indicating paints, see Horiguchi et al., Sci. Papers Inst. Phys. Chem. Research (Tokyo), Volume 53, pp. 274–283, published 1959 and Adbo, U.S. Pat. No. 3,352,794. The thermochromic systems are handicapped by one of more problems such as a dark initial color, low intensity color formation, slow rate of response to heat, slow discharge of color on the removal of the heat source, deterioration of the compounds after several thermal cycles or exposure to ultraviolet, or by attack by moisture or other environmental impurities, a requirement for a specific medium such as solvents in order to function, or extremely high costs.

These deficiencies are generally overcome by the present invention. The compositions of this invention may be used as a powder, or compressed into pellet form or dispersed in a film forming vehicle and applied as a coating. The compositions of this invention are light colored at normal or ambient temperatures and are capable of being rapidly converted to an intense color on application of heat. This heat generated color is rapidly discharged on removal of the heat source. These color cycles can be repeated many times without apparent loss of response to heat and cooling.

One objective of this invention is the production of reactive compositions which rapidly form a color when heated and return to their original color on removal of the heat source.

A second objective of this invention is to provide compositions for temperature indicators, thermal display media, safety papers, and verification or validation devices.

These objectives are accomplished by combining 3,3-bis (aminophenyl) phthalides with organic acids. The phthalides of this invention will normally form a color on direct contact with an acid. However, it has been discovered that certain types of acids will react with the phthalides to form a color only when heated, and this composition will revert to the original color upon cooling. It has also been discovered that the acids used in this invention will react in this thermal color reversal manner with only certain classes of phthalides.

The phthalides useful in this invention are derivatives of 3,3-bis(aminophenyl)phthalide in which the amine substituent may be a primary, secondary, or tertiary amine. Additional groups may be included in the phenyl radicals and/or on the aromatic ring of the phthalide radical.

Phthalides which are useful in this invention are described by Adams, U.S. Pat. No. 2,417,897, U.S. Pat. No. 2,443,092, U.S. Pat. No. 2,474,084 and U.S. Pat. No. Re. 23,024; Green et al., U.S. Pat. No. 2,646,367, and Oda et al., U.S. Pat. No. 3,389,007. These phthalides have been described as forming colored products on contact with acidic materials. However, these phthalides react with the specific acids of this invention to give thermally reversible color systems.

Acids suitable for incorporation in the heat-sensitive compositions of the present invention are listed in Table I, and phthalides which have been found to give reversible color formation with 5-bromosalicylic acid are listed in Table II. It is expected that combinations of other homologous and nonhomologous acids and phthalides may also produce colors reversibly. Numerous other phthalides are listed in co-pending U.S. patent application Ser. Nos. 772,084 filed Feb. 25, 1977 for HEAT SENSITIVE RECORDING COMPOSITION WITH COMPLEXED PHENOLICS; and Ser. No. 774,385 filed Mar. 4, 1977 for HEAT-SENSITIVE RECORDING COMPOSITION WITH MIXED COLOR PRECURSORS.

Activators which are useful for lowering the temperature of color formation of the phthalide-acid combinations include sulfonamides such as benzene sulfonamide, p-toluene sulfonamide, and other sulfonamide homologs.

The mechanism for thermal reversible color formation is uncertain. It is suspected that the acid radical forms a salt with one of the available amine radicals of the phthalide and the other available amine radical from the phthalide forms a hydrogen bond with the —SH or —OH group of the acid, and that the equilibrium of the hydrogen bonding reaction is temperature dependent.

In accordance with this invention, finely divided particles of a 3,3-bis(aminophenyl)phthalide are mechanically united with finely divided particles of an organic acid containing hydroxyl or thiol groups. This composition may be applied as a powder to a substrate or the particles may be dispersed in a binder vehicle and applied as a coating to the substrate. Application of heat to the resulting structure will cause formation of a contrasting color which reverts to the original color of the mixture upon removal of the heat source.

The operation of this invention may be illustrated by the following test procedure. Equal portions by weight of the phthalide and the organic acid are ground together in a mortar and pestle to obtain an intimate mixture of the co-reactants. The powder thus obtained is spread onto paper as a thin layer by use of a spatula or other suitable means. A hot plate is set at a desired activation temperature. A suitable temperature for verification of color change is 177° C. The reactant coated paper is placed in contact with the heated surface of the hot plate. If a color change occurs which reverts to the original color on cooling, the composition is regarded as fulfilling the requirements of the invention. Table I, examples 1 to 18, gives a list of acids tested with 3,3-bis(p-aminophenyl)phthalide. Table II, examples 19 to 31, indicates phthalides which give a positive test with 5-bromosalicylic acid. The 5-bromosalicylic acid could have been replaced with any acid from Table I and still would show a positive reaction. It should be recognized that the ratio of reactants is not critical as the phthalide/acid ratio was varied from 1/5 to 5/1 to give thermally reversible color changes in all cases.

Thermally color-reversible coated sheets were prepared in the following manner. A composition of equal parts 3,3-bis(p-aminophenyl)phthalide, ethyl hydroxyethylcellulose, and toluene was ball milled and coated onto paper to give a dry coating weight of 5 pounds per 3000 square feet. The dried coated sheet was then topcoated (5 pounds per 3000 square feet) with a ball mill grind containing equal parts of acid/ethylhydroxyethylcellulose/toluene. The dried coated sheets were then tested by contacting for one second with hot plates set at different activation temperatures. The activation temperature of each combination was obtained and recorded in Table III. All examples returned to their initial color almost immediately after removal from the hot plate. All systems were tested through 10 cycles of thermal color formation and reversal without any noticeable deterioration of response. Other resin binders used in similar tests included glue in water, polyvinylpyrrolidone in solvent, and polyvinylalcohol in water. Specific binder systems are not required to provide the reversal system and the reactants will perform in a similar manner even without a binder present.

TABLE I

| | (with 3,3-bis (p-aminophenyl) phthalide) | |
|---|---|---|
| Example | Acid | Color |
| 1. | salicylic | dark violet |
| 2. | 5-bromo salicylic | blue violet |
| 3. | 5-chlorosalicylic | strong blue |
| 4. | 3,5-dinitrosalicylic | green-black |
| 5. | 3,5-dichlorosalicylic | blue |
| 6. | thiosalicylic | blue |
| 7. | 3-nitrosalicylic | green-black |
| 8. | 5-nitrosalicylic | blue |
| 9. | 5-methylsalicylic | blue |
| 10. | 5-methoxysalicylic | blue |
| 11. | 3,5-dibromosalicylic | blue |
| 12. | 1-hydroxy-2-naphthoic | blue |
| 13. | 2,3-dihydroxybenzoic | blue-black |
| 14. | 2,6-dihydroxybenzoic | dark blue |
| 15. | 2-hydroxy-5-methoxybenzoic | blue |
| 16. | benzilic | blue violet |
| 17. | diglycolic | blue |
| 18. | dithiodiglycolic | violet |

The following derivatives either gave a permanent color or no color when heated in combination with 3,3-bis(p-aminophenyl)phthalide; 1-naphthoic acid, 5-nitrosalicylaldehyde, pyrogallol, 3,5-dihydroxybenzoic acid, o-toluic acid, m-toluic acid, p-toluic acid, 4-hydroxy-3-methoxybenzoic acid, 5-amino-2-hydroxybenzoic acid, 4-diethylaminosalicylic acid, 4-amino salicylic acid.

TABLE II

| | (with 5-bromosalicylic acid) | |
|---|---|---|
| Example | Phthalide | Color |
| 2. | 3,3-bis(p-aminophenyl) | blue-violet |
| 19. | 3,3-bis(p-dimethylaminophenyl)-5-dimethylamino | " |
| 20. | 3,3-bis(p-dimethylaminophenyl)-5-amino | " |
| 21. | 3,3-bis(p-dimethlaminophenyl)-6-dimethylamino | " |
| 22. | 3,3-bis(p-dimethylaminophenyl) | " |
| 23. | 3,3-bis(p-dimethylaminophenyl) | " |
| 24. | 3,3-bis(p-di-n-propylaminophenyl) | " |
| 25. | 3,3-bis(4-dimethylamino-3-methylphenyl) | " |
| 26. | 3,3-bis(p-dimethylaminophenyl)-4,5,6,7-tetrachloro | " |
| 27. | 3,3-bis(p-diethylaminophenyl)-6-diethylamino | " |
| 28. | 3,3-bis(p-ethylaminophenyl) | " |
| 29. | 3,3-bis(p-methylaminophenyl) | " |
| 30. | 3,3-bis(p-benzylaminophenyl) | " |

TABLE II-continued

| | (with 5-bromosalicylic acid) | |
|---|---|---|
| Example | Phthalide | Color |
| 31. | 3,3-bis(p-chloromethylaminophenyl) | " |

Other leuco color formers which provided either a permanent color or no color include: phenolphthalein; tetramethylbenzidine; o-hydroxybenzalacetophenone; 4'-(p-dimethylaminophenylazo)benzanilide; benzoyl leuco methylene blue; xantheni-9,o-benzoic acid 3,6-bis-(dimethylamino)-9-p-nitroanilino lactam; naphthoyl leuco methylene blue; 10-(chlorobenzoyl)-3,7-bis(o-dimethylamino) phenothiazine; phthalide; and benzalphthalide.

TABLE III

| Coatings Containing 3,3-bis (p-aminophenyl) phthalide and Acids | | |
|---|---|---|
| Example | Acid | Activation Temperature (1 sec.) |
| 32. | Thiosalicylic | 149° C. |
| 33. | 3-nitrosalicylic | 121° C. |
| 34. | 5-nitrosalicylic | 121° C. |
| 35. | 5-bromosalicylic | 121° C. |
| 36. | 3,5-dichlorosalicylic | 121° C. |
| 37. | 2,3-dihydroxybenzoic | 121° C. |
| 38. | 3,5-dibromosalicylic | 121° C. |
| 39. | 5-methylsalicylic | 132° C. |
| 40. | 5-methoxysalicylic | 121° C. |
| 41. | benzilic | 121° C. |
| 42. | 2,6-dihydroxybenzoic | 121° C. |
| 43. | 2-hydroxy-5-methoxybenzoic | 149° C. |

While the present invention has been described with reference to several preferred embodiments, various changes and modifications may be made therein without departing from the invention. The following claims are intended to cover all such changes, modifications and equivalent ingredients which fall within the spirit and scope of the invention.

What is claimed is:

1. A heat-sensitive color-reversing composition comprising
(a) a 3,3-bis(p-aminophenyl)phthalide selected from the group consisting of
   3,3-bis(p-aminophenyl)phthalide,
   3,3-bis(p-dimethylaminophenyl)-5-dimethylamino phthalide,
   3,3-bis(p-dimethylaminophenyl)-5-amino phthalide,
   3,3-bis(p-dimethylaminophenyl)-6-dimethylamino phthalide,
   3,3-bis(p-dimethylaminophenyl)phthalide,
   3,3-bis(p-diethylaminophenyl)phthalide,
   3,3-bis(p-di-n-propylaminophenyl)phthalide,
   3,3-bis(4-dimethylamino-3-methylphenyl)phthalide,
   3,3-bis(p-dimethylaminophenyl)-4,5,6,7-tetrachloro phthalide,
   3,3-bis(p-diethylaminophenyl)-6-diethylamino phthalide,
   3,3-bis(p-ethylaminophenyl)phthalide,
   3,3-bis(p-methylaminophenyl)phthalide,
   3,3-bis(p-benzylaminophenyl)phthalide, and
   3,3-bis(p-chloromethylaminophenyl)phthalide;
(b) an organic acid selected from the group consisting of
   thiosalicylic acid,
   3-nitrosalicylic acid,
   5-nitrosalicylic acid,
   5-bromosalicylic acid,
   3,5-dichlorosalicylic acid, 2,3-dihydroxybenzoic acid,
3,5-dibromosalicylic acid,
5-methylsalicylic acid,
5-methoxysalicylic acid, benzilic acid,
2,6-dihydroxybenzoic acid,
2-hydroxy-5-methoxybenzoic acid,
5-chlorosalicylic acid,
3,5-dinitrosalicylic acid,
1-hydroxy-2-naphthoic acid,
diglycolic acid, and
dithiodiglycolic acid;
said color-reversing composition being characterized in that it develops a color contrasting visibly with its original color upon heating, and returns to its original color upon cooling.

2. The heat-sensitive composition of claim 1, wherein said 3,3-bis(p-aminophenyl)phthalide is 3,3-bis(p-aminophenyl)phthalide.

3. The heat-sensitive composition of claim 1, wherein said organic acid is 5-bromosalicylic acid.

4. The heat-sensitive composition of claim 1 dispersed as a pigment in a binder solution.

5. A substrate coated with a single layer of the composition of claim 4.

6. The heat-sensitive composition of claim 1, and further comprising an activator reducing the temperature at which color is formed upon heating.

7. The composition of claim 6, wherein said activator comprises an aromatic sulfonamide.

8. The composition of claim 7, wherein said activator is selected from the group consisting of benzene sulfonamide and p-toluene sulfonamide.

* * * * *